US010667502B2

(12) United States Patent
Wu et al.

(10) Patent No.: US 10,667,502 B2
(45) Date of Patent: Jun. 2, 2020

(54) LARGE-SCALE AND MULTI-SPAN BREEDING GREENHOUSE FOR ADULT BLACK SOLDIER FLIES

(71) Applicant: Guangzhou Unique Biotechnology Co., Ltd., Guangzhou, Guangdong (CN)

(72) Inventors: Yuan Wu, Guangdong (CN); Wenfeng Hu, Guangdong (CN); Xu Pang, Guangdong (CN); Chujun Li, Guangdong (CN); Dou Hu, Guangdong (CN)

(73) Assignee: Guangzhou Unique Biotechnology Co., Ltd., Guangzhou (CN)

( * ) Notice: Subject to any disclaimer, the term of this patent is extended or adjusted under 35 U.S.C. 154(b) by 201 days.

(21) Appl. No.: 16/041,756

(22) Filed: Jul. 21, 2018

(65) Prior Publication Data

US 2019/0110451 A1    Apr. 18, 2019

(30) Foreign Application Priority Data

Oct. 18, 2017  (CN) ..................... 2017 2 1349251 U

(51) Int. Cl.
*A01K 67/033*         (2006.01)
(52) U.S. Cl.
CPC ...... *A01K 67/033* (2013.01); *A01K 2227/706* (2013.01)
(58) Field of Classification Search
CPC .... A01K 67/033; A01K 29/005; A01K 29/00; A01K 2227/706; A01K 49/00; A01G 31/02; A01G 9/14
USPC .................................. 119/6.5, 6.6, 174, 421
See application file for complete search history.

(56) References Cited

U.S. PATENT DOCUMENTS

| | | | | |
|---|---|---|---|---|
| 5,158,497 A * | 10/1992 | Rossignol | ............... | A01K 49/00 119/6.5 |
| 5,351,643 A * | 10/1994 | Hughes | ................ | A01K 67/033 119/6.5 |
| 6,938,574 B2 * | 9/2005 | Zhang | .................. | A01K 67/033 119/6.5 |
| 8,408,164 B2 * | 4/2013 | Robinson, Jr. | ........ | A01K 67/033 119/174 |
| 9,462,795 B2 * | 10/2016 | Chin | .................... | A01K 67/033 |
| 9,642,344 B2 * | 5/2017 | Unger | .................. | A01K 67/033 |
| 10,051,845 B1 * | 8/2018 | Massaro | ............. | A01K 67/033 |

(Continued)

*Primary Examiner* — Yvonne R Abbott-Lewis

(57) ABSTRACT

The present invention discloses a large-scale and multi-span breeding greenhouse for adult black soldier flies, comprising greenhouse bodies. Each greenhouse body comprises a pupae room and a mating and oviposition room; a partition wall is provided between the pupae room and the mating and oviposition room, the partition wall is provided with a door hole communicating the pupae room and the mating and oviposition room; the pupae room is opaque; the greenhouse body further comprises a light guiding device which introduces sunlight into the mating and oviposition room. The present invention provides a suitable growth and breeding environment, ensures a high reproduction rate, and can achieve large-scale captive breeding of black soldier flies. The greenhouse has a high level of automation and can be easily cleaned and maintained. Little human interference takes place in the breeding process, no random oviposition is observed, and the egg collection rate is high.

11 Claims, 3 Drawing Sheets

(56) References Cited

U.S. PATENT DOCUMENTS

| | | | |
|---|---|---|---|
| 10,405,528 B2* | 9/2019 | Comparat | B65G 1/0414 |
| 2014/0020630 A1* | 1/2014 | Courtright | A01K 29/00 |
| | | | 119/6.6 |
| 2015/0122182 A1* | 5/2015 | Aldana | A01K 67/033 |
| | | | 119/6.6 |
| 2015/0245569 A1* | 9/2015 | Villamar | A01G 31/02 |
| | | | 119/227 |
| 2015/0296760 A1* | 10/2015 | Perednia | A01K 67/033 |
| | | | 119/6.5 |
| 2016/0066552 A1* | 3/2016 | Arsiwalla | A01K 67/0332 |
| | | | 119/6.5 |
| 2016/0219887 A1* | 8/2016 | Vickerson | A01M 1/106 |
| 2017/0202191 A1* | 7/2017 | Marchant | A01K 67/033 |

* cited by examiner

LARGE-SCALE AND MULTI-SPAN BREEDING GREENHOUSE FOR ADULT BLACK SOLDIER FLIES

CROSS REFERENCE TO RELATED APPLICATIONS

The present application claims the benefit of Chinese Utility Model Application No. 201721349251.6 filed on Oct. 18, 2017. All the above are hereby incorporated by reference.

FIELD OF THE INVENTION

The present invention relates to an insect breeding greenhouse and, in particular, to a large-scale and multi-span breeding greenhouse for adult black soldier flies.

BACKGROUND OF THE INVENTION

The black soldier fly, also known as *Hermertia illucens* L., is a dipterous, saprophytic insect that can be used to decompose a variety of organic wastes and scraps. It is also an edible or feeding insect recommended by the United Nations. In the wild, black soldier flies live in tropical and subtropical areas. Their prepupae prefer to pupate at sites that are dry, shady and close to water sources. After emergence, they usually mate on sunny mornings and lay eggs in dry gaps close to food sources.

As a kind of economic insect, the captive breeding of black soldier flies have been continuously explored in order to achieve large-scale breeding. Initially, people merely used insect cages for the captive breeding of black soldier flies. Although insect cages provide relatively independent spaces for the mating and oviposition of black soldier flies, space limitations are too great for large-scale breeding. For this reason, a kind of breeding greenhouse for adult black soldier flies, which mimics a greenhouse for vegetables, has been developed. Although these breeding greenhouses adult soldier flies offer improvements in terms of space, they have the following problems:

1. Plants, which are placed on the floor, are employed to increase the surface area for attachments of adult black soldier flies. This causes difficulties in the cleaning and maintenance of the breeding greenhouses. Furthermore, many eggs of the black soldier flies are directly laid on the plants, causing difficulties in egg collection.

2. Due to problems in building materials and structural design, the inside of these breeding greenhouses tend to have problems such as excessively high temperature, poor ventilation, and difficulties in light intensity control. These problems have serious impacts on the survival and breeding of black soldier flies.

3. Adult black soldier flies tend to lay eggs in various locations, and many eggs are directly laid on pupae shells of black soldier flies or on the floor, and the egg collection rate is low. Therefore, it is still difficult to achieve large-scale breeding of black soldier flies.

SUMMARY OF THE INVENTION

The objective of the present invention is to overcome the shortcomings of the prior art and to provide a large-scale and multi-span breeding greenhouse for adult black soldier flies, in order to achieve the large-scale captive breeding of black soldier flies.

The technical solution of the present invention is: a large-scale and multi-span breeding greenhouse for adult black soldier flies, comprising greenhouse bodies, each greenhouse body comprises a pupae room and a mating and oviposition room; a partition wall is provided between the pupae room and the mating and oviposition room, the partition wall is provided with a door hole communicating the pupae room and the mating and oviposition room; the pupae room is opaque; the greenhouse body further comprises a light guiding device which introduces sunlight into the mating and oviposition room.

The pupae room of the present invention is used for placing the prepupae of black soldier flies. Preferably, a shelf can be placed inside the pupae room, and the prepupae of black soldier flies can be placed on the shelf. The partition wall allows the formation of two spaces within the mating and oviposition room and the pupae room, which are relatively independent and do not interfere with each other. Adult black soldier flies are phototactic, hence after the prepupae in the pupae room become adult black soldier flies, they would fly through the door hole towards the luminous mating and oviposition room. In this way, the need for manual relocation of pupae in the prior art can be reduced, and excessive interference with the black soldier flies can be avoided, which is better for the reproduction of black soldier flies. The light guiding device ensures enough sunlight penetrates into the mating and oviposition room to provide a mating environment that is close to natural conditions for adult black soldier flies.

Furthermore, a wall of the greenhouse bodies is consisted of a color steel plate, film or a cement brick wall. In this way, the wall could play a role in sun protection, heat preservation, and moisture retention. It not only ensures that the pupae room is not light-penetrating, but also ensures that the mating and oviposition room has a shady area for the adult black soldier flies, preventing them from being sunburned.

Furthermore, the wall of the greenhouse body comprises a first wall and a second wall, the first wall forms a wall of the mating and oviposition room with the partition wall, the second wall forms a wall of the pupae room with the partition wall.

Preferably, the light guiding device comprises a light transmitting window, which is arranged on the first wall, and light transmitting boards, which are embedded on a roof of the mating and oviposition room; the inside of the light transmitting window is provided with a detachable gauze; the light transmitting boards are arranged disjointedly. The gauze could prevent the adult black soldier flies from flying out of the mating and oviposition room, its detachable structure allows easy cleaning. The disjointed arrangement of the light transmitting boards ensures that the mating and oviposition room has enough sunlight as well as shady areas for the adult black soldier flies.

Preferably, the light guiding device comprises an auto-tracking reflector, which reflects sunlight into the mating and oviposition room, and/or a light guiding lighting system, which introduces sunlight into the mating and oviposition room. The auto-tracking reflector consists of a sunlight tracker and a reflector of the prior art; the light guiding lighting system is of the prior art, and comprises a lighting device, a light guiding device and a diffusion device.

The automatic tracking reflector consists of an existing solar tracker and an existing reflector; the light guide lighting system is an existing light guide lighting system, and its structure includes a lighting device, a light guide device and a light diffusion device.

Preferably, the mating and oviposition room is provided with an egg collecting device and an attaching material for the attachment of black soldier flies.

Furthermore, the egg collecting device comprises a stand, an oviposition plate provided on the stand, and an oviposition-inducing material placed on the oviposition plate. The scent is a chief clue for adult black soldier flies in the search of an oviposition spot. The scent emitted by the oviposition-inducing material could induce the oviposition of black soldier flies on the oviposition plate. This facilitates the collection of black soldier flies' eggs and prevents random oviposition.

Furthermore, the attaching material is an artificial plant and/or cloth and/or fibrous stripe suspended in the mating and oviposition room. The attaching material of the present invention is not limited to this and may be any stripe for the attachment of insects. In this invention, the practice of the prior art, which involves placing plotted green plants on the floor to provide attachment for black soldier flies, has been abandoned. Instead, a stripe that can be repeatedly used, such as an artificial plant and/or cloth and/or fibrous stripe, is employed and suspended in the mating and oviposition room for the attachment of black soldier flies. This is not only convenient for cleaning and maintenance but also low in cost and reduces occupation of floor area. Furthermore, the attachment material of the present invention is not affected by climate and has a long lifespan. On the contrary, green plants are affected by climate, life cycles, et cetera; therefore, they need to be replaced frequently. They also occupy floor space and obstruct floor cleaning.

Furthermore, the greenhouse body is further provided with a temperature and humidity control system, which comprises a shading net to control the light transmitting area of the light transmitting window and the light transmitting board, a negative pressure exhaust fan installed on the first wall, a radiator installed in the pupae room and the mating and oviposition room, a first spraying device and an air conditioner both installed in the mating and oviposition room, and a second spraying device installed above the greenhouse body. When the temperature inside the greenhouse body is too high or the humidity is too low, the temperature may be lowered by the first spraying device and the second spraying device, and the humidity may be increased by the second spraying device. The present invention is more convenient, effective and cleaner than manual water spraying of the prior art. The first spraying device can also be used to replenish drinking water for adult black soldier flies, thereby reducing the level of interference caused by manual water replenishment. In the present invention, the light transmitting area of the light transmitting plate and the light transmitting window could be flexibly adjusted by the shading net, thereby controlling the intensity of light transmitted into the mating and oviposition room and providing a comfortable living environment for the black soldier flies. Preferably, negative pressure exhaust fans are all installed on the same wall surface of the first wall and away from the door hole. Ventilation in the mating and oviposition room can be achieved through the light transmitting window and the negative pressure exhaust fan. When the negative pressure exhaust fan is turned on, negative pressure is formed, and indoor air flows towards the direction of the negative pressure exhaust fan. In this way, the oviposition-inducing material in the egg collecting device would give a clear scent trail; its scent would not flow into the pupae room, thereby preventing adult black soldier flies from flying into the pupae room to lay eggs, preventing random oviposition.

Furthermore, the greenhouse bodies are arranged in an annular array or in a row, and the greenhouse bodies are either connected to each other or arranged disjointedly. When the greenhouse bodies are in an annular array, their pupae rooms are located in the inner periphery of the greenhouse bodies. This ensures that the mating and oviposition rooms have plenty of sunlight.

The breeding greenhouse further comprises a buffer room which is connected to the pupae room, the buffer room is either provided inside the greenhouse body or between two greenhouse bodies. When the buffer room is provided in the greenhouse body, each greenhouse body is independently provided with a buffer room which is connected to its pupae room. When the buffer room is located between two greenhouse bodies, the two adjacent greenhouse bodies share the same buffer room. In this way, the number of buffer rooms can be reduced, the area of the mating and oviposition room can be increased accordingly, and construction cost can be lowered. As a transition room, the buffer room can be used for sanitation preparations (such as disinfection) before the staffs enter the pupae room, thereby preventing external bacteria and other pollutants from being brought into the mating and oviposition room or the pupae room, safeguarding the healthy growth and propagation of black soldier flies.

Comparing with the prior art, the beneficial effects of the present invention are as follows:

The large-scale and multi-span breeding greenhouse for adult black soldier flies has a high level of automation and can be easily cleaned and maintained. Furthermore, little human interference takes place in the breeding process, no random oviposition is observed, and the egg collection rate is high. The present invention provides a suitable growth and breeding environment for black soldier flies, ensures a high reproduction rate, and can achieve the large-scale captive breeding of black soldier flies.

Figure 1:
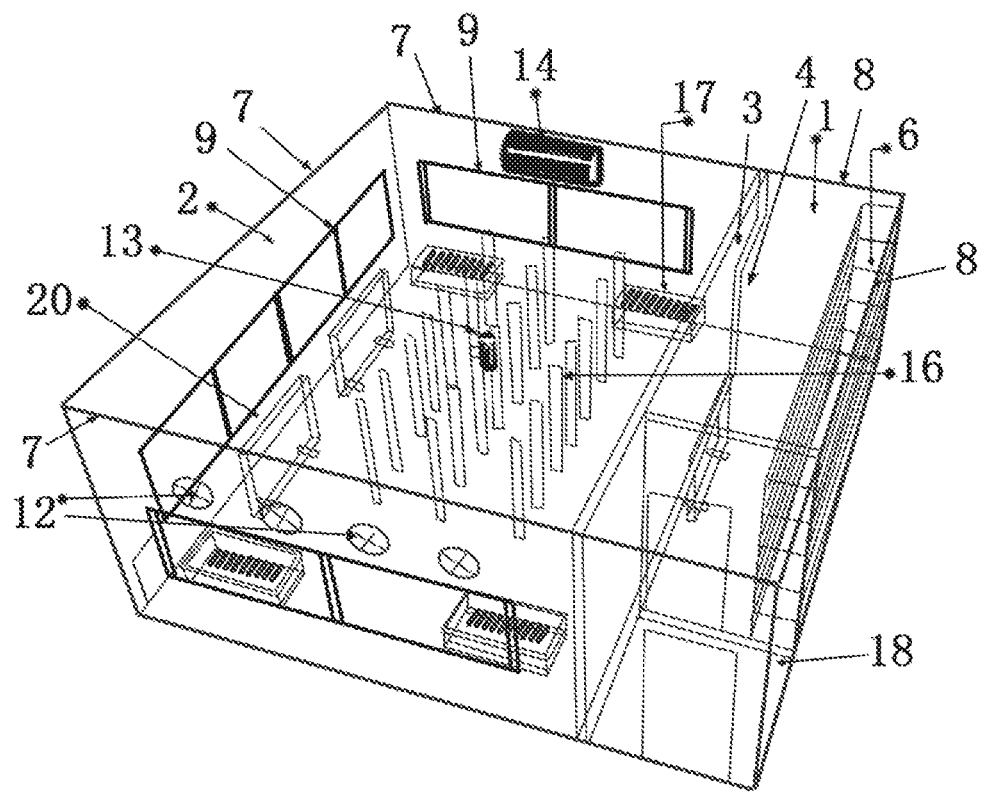
FIG. 1 is a perspective drawing of the internal structure of the greenhouse body according to embodiment 1 of the present invention.

In the figures: pupae room 1, mating and oviposition room 2, partition wall 3, door hole 4, light guiding device 5, shelf 6, first wall 7, second wall 8, light transmitting window 9, roof 10, light transmitting board 11, negative pressure exhaust fan 12, first spraying device 13, air conditioner 14, second spraying device 15, attaching material 16, egg collecting device 17, buffer room 18, buffer room 19, radiator 20, light guiding device 21, light transmitting window 22, auto-tracking reflector 23, light guiding device 24, light transmitting window 25, light guide lighting system 26, pupae room 27, mating and oviposition room 28.

DETAILED DESCRIPTION OF THE ILLUSTRATED EMBODIMENTS

To better illustrate the purpose, technical solutions and advantages of the present invention, the present invention is further described below in combination with the accompanying drawings and specific embodiments.

Embodiment 1

Figure 2:
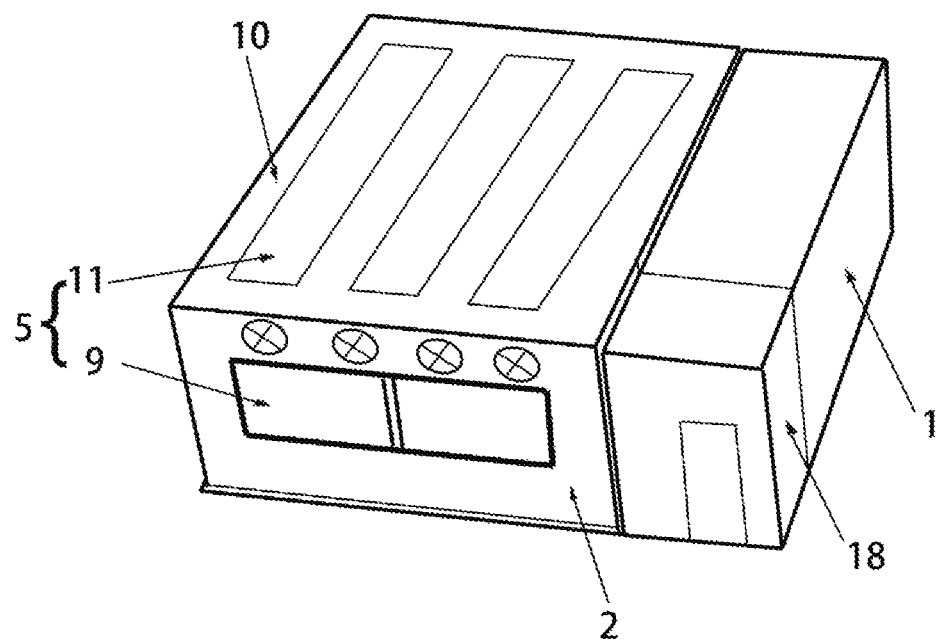
FIG. 2 is a schematic diagram of the external structure of the greenhouse body according to embodiment 1 of the present invention.
Figure 3:
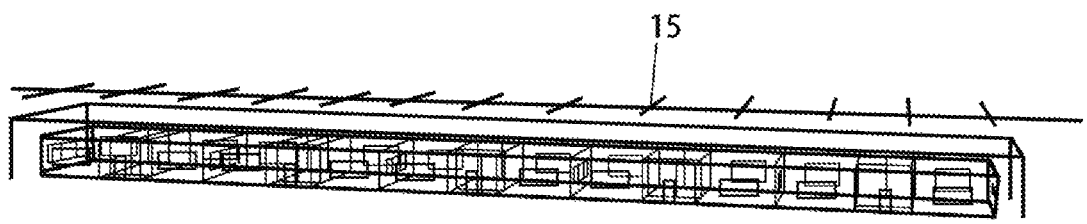
FIG. 3 is a schematic diagram of the overall structure of the breeding greenhouse according to embodiment 1 of the present invention.

Embodiment 1 provides a large-scale and multi-span breeding greenhouse for adult black soldier flies, comprising greenhouse bodies. As shown in FIG. 1-FIG. 3, each greenhouse body comprises a pupae room 1 and a mating and oviposition room 2; a partition wall 3 is provided between the pupae room and the mating and oviposition room, the partition wall is provided with a door hole 4 communicating the pupae room and the mating and oviposition room. The partition wall allows the formation of two spaces within the mating and oviposition room and the pupae room, which are relatively independent and do not interfere with each other. Adult black soldier flies are phototactic, hence after the prepupae in the pupae room become adult black soldier flies, they would fly through the door hole towards the luminous mating and oviposition room. In this way, the need for manual relocation of pupae in the prior art can be reduced, and excessive interference with the black soldier flies can be avoided, which is better for the reproduction of black soldier flies.

Specifically, the pupae room is used for placing the prepupae of black soldier flies. The pupae room is opaque. A shelf 6 is placed inside the pupae room, and the prepupae of black soldier flies can be placed on the shelf.

Specifically, a wall of the greenhouse bodies consists of a color steel plate, film or a cement brick wall. In this way, the wall could play a role in sun protection, heat preservation, and moisture retention. It not only ensures that the pupae room is not light-penetrating, but also ensures that the mating and oviposition room has a shady area for the adult black soldier flies, preventing them from being sunburned.

Specifically, the wall of the greenhouse body comprises a first wall 7 and a second wall 8, the first wall forms a wall of the mating and oviposition room with the partition wall, the second wall forms a wall of the pupae room with the partition wall.

Specifically, as adult black soldier flies usually mate on sunny mornings, the greenhouse also includes a light guiding device 5 which introduces sunlight into the mating and oviposition room, allowing the penetration of sufficient sunlight into the mating and oviposition room, providing a mating environment that is close to natural conditions for the black soldier flies. The light guiding device comprises a light transmitting window 9, which is arranged on the first wall, and light transmitting boards 11, which are embedded on a roof 10 of the mating and oviposition room; the inside of the light transmitting window is provided with a detachable gauze; the light transmitting boards are arranged disjointedly. When the light transmitting window is opened, the gauze could prevent the adult black soldier flies from flying out of the mating and oviposition room. The detachable structure of the gauze allows easy cleaning. The disjointed arrangement of the light transmitting boards ensures that the mating and oviposition room has enough sunlight as well as shady areas for the adult black soldier flies.

Specifically, the mating and oviposition room is provided with an egg collecting device 17 and an attaching material 16 for the attachment of black soldier flies. The egg collecting device comprises a stand, an oviposition plate provided on the stand, and an oviposition-inducing material placed on the oviposition plate. The scent is a chief clue for adult black soldier flies in the search of an oviposition spot. The scent emitted by the oviposition-inducing material could induce the oviposition of black soldier flies on the oviposition plate. This facilitates the collection of black soldier flies' eggs and prevents random oviposition. The attaching material of the present embodiment is artificial plants suspended in the mating and oviposition room. Of course, the attaching material of the present embodiment is not limited to this, and may be any stripe for the attachment of black soldier flies, for example cloth stripes or ribbons. In this embodiment, the practice of the prior art, which involves placing plotted green plants on the floor to provide attachment for black soldier flies, has been abandoned. Instead, artificial plants or stripes that can be repeatedly used are employed and suspended in the mating and oviposition room for the attachment of black soldier flies. This is not only convenient for cleaning and maintenance but also low in cost and reduces occupation of floor area. Furthermore, the attachment material of the present invention is not affected by climate and has a long lifespan. On the contrary, green plants are affected by climate, life cycles, et cetera; therefore, they need to be replaced frequently. They also occupy floor space and obstruct floor cleaning.

Furthermore, the greenhouse body is also provided with a temperature and humidity control system, which comprises a shading net to control the light transmitting area of the light transmitting window and the light transmitting board, a negative pressure exhaust fan 12 installed on the first wall, a radiator 20 installed in the pupae room and the mating and oviposition room, a first spraying device 13 and an air conditioner 14 both installed in the mating and oviposition room, and a second spraying device 15 installed above the greenhouse body. When the temperature inside the greenhouse body is too high or the humidity is too low, the temperature may be lowered by the first spraying device and the second spraying device, and the humidity may be increased by the second spraying device. When the temperature inside the greenhouse body is too low, the room temperature can be raised by the radiator. Meanwhile, the air conditioner can also be used to regulate room temperature and humidity. The temperature and humidity control system is more convenient, hygienic and effective than manual temperature and humidity control methods of the prior art, such as manual water spraying. The first spraying device can also be used to replenish drinking water for adult black soldier flies, thereby reducing the level of interference caused by manual water replenishment. In the present invention, the light transmitting area of the light transmitting plate and the light transmitting window could be flexibly adjusted by the shading net, thereby controlling the intensity of light transmitted into the mating and oviposition room and providing a comfortable living environment for the black soldier flies. In the present embodiment, negative pressure exhaust fans are all installed on the same wall surface of the first wall and away from the door hole. Ventilation in the mating and oviposition room can be achieved through light transmitting windows and negative pressure exhaust fans. When the negative pressure exhaust fans are turned on, negative pressure is formed, and indoor air flows towards the direction of the negative pressure exhaust fans. In this way, the oviposition-inducing material in the egg collecting device would give a clear scent trail; its scent would not flow into the pupae room, thereby preventing adult black soldier flies from flying into the pupae room to lay eggs, preventing random oviposition.

In the present embodiment, the greenhouse bodies are arranged in a row, and the greenhouse bodies are arranged disjointedly. The breeding greenhouse further independently comprises a buffer room 18 which is connected to the pupae room. As a transition room, the buffer room can be used for sanitation preparations (such as disinfection) before the staffs enter the pupae room, thereby preventing external bacteria and other pollutants from being brought into the mating and oviposition room or the pupae room, safeguarding the healthy growth and propagation of black soldier flies.

Embodiment 2

Figure 4:
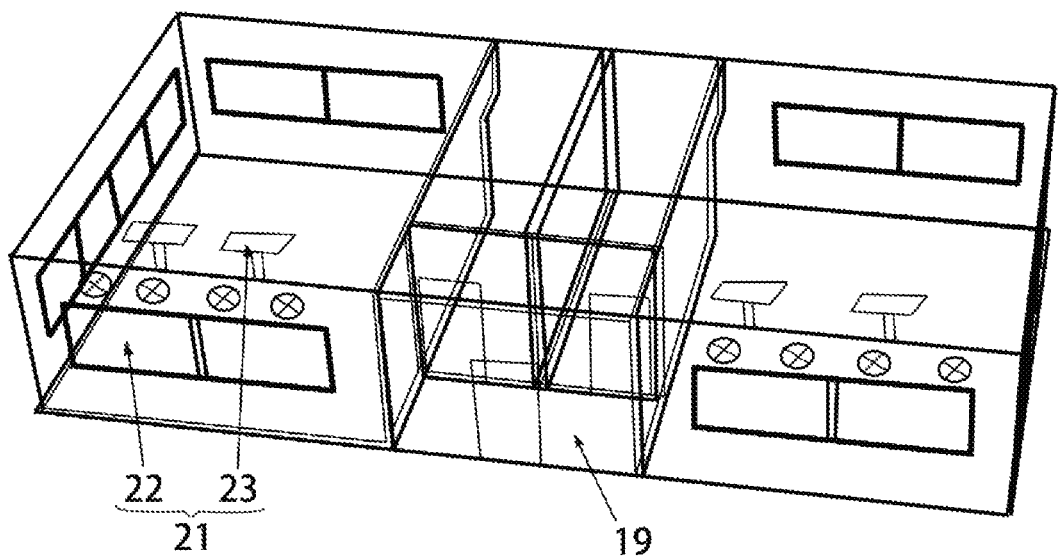
FIG. 4 is a schematic diagram showing the greenhouse bodies connecting to each other according to embodiment 2 of the present invention.

Embodiment 2 provides a large-scale and multi-span breeding greenhouse for adult black soldier flies. Embodiment 2 is modified on the basis of embodiment 1. The differences between embodiment 2 and embodiment 1 are in the structure of the light guiding device, the arrangement of greenhouse bodies, and the arrangement of buffer rooms, the details of which are described as follows:

In embodiment 2, as shown in FIG. 4, the light guiding device 21 comprises a light transmitting window 22, which is arranged on the first wall, and an auto-tracking reflector 23, which is installed outside the mating and oviposition room. The inside of the light transmitting window is provided with a detachable gauze. The auto-tracking reflector could reflect sunlight into the mating and oviposition room. The auto-tracking reflector of this embodiment is prior art, and therefore will not be described in detail here. When the light transmitting window is opened, the gauze could prevent adult black soldier flies from flying out of the mating and oviposition room. The gauze is detachable and easy to clean.

In embodiment 2, as shown in FIG. 4, a buffer room 19 is provided between two adjacent greenhouse bodies and is connected to the pupae rooms of these two greenhouse bodies. In this way, the number of buffer rooms can be reduced, the area of the mating and oviposition room can be increased accordingly, and construction cost can be lowered.

In embodiment 2, as shown in FIG. 4, the greenhouse bodies are connected to each other, and they are arranged in an annular array.

Embodiment 3

Figure 5:
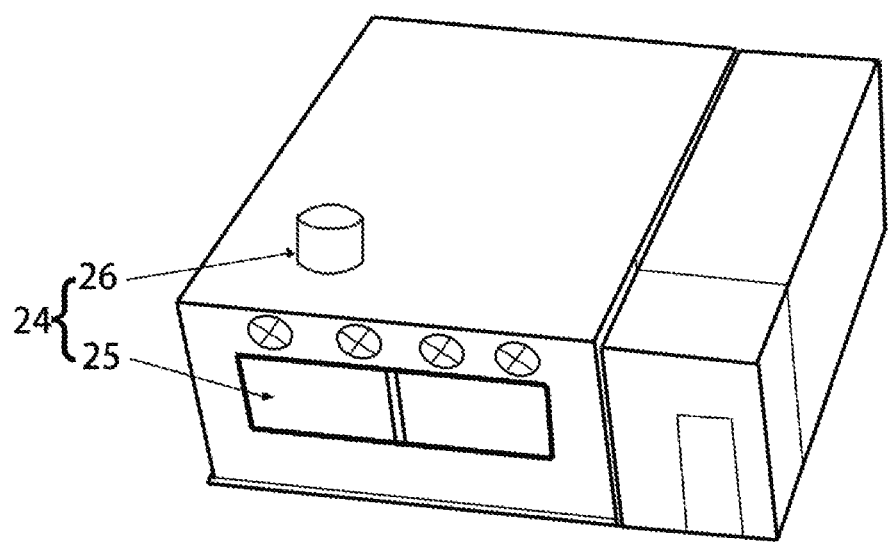
FIG. 5 is a schematic diagram of the external structure of the greenhouse body according to embodiment 3 of the present invention.

Embodiment 3 provides a large-scale and multi-span breeding greenhouse for adult black soldier flies. Embodiment 3 is modified on the basis of embodiment 1. The differences between embodiment 3 and embodiment 1 are in the structure of the light guiding device and the arrangement of greenhouse bodies, the details of which are described as follows:

In embodiment 3, as shown in FIG. 5, the light guiding device 24 comprises a light transmitting window 25, which is arranged on the first wall, and a light guide lighting system 26, which is installed on the roof of the mating and oviposition room. The inside of the light transmitting window is provided with a detachable gauze. The light guide lighting system could introduce sunlight into the mating and oviposition room. The light guide lighting system of embodiment 3 is prior art, and therefore will not be described in detail here.

Figure 6:
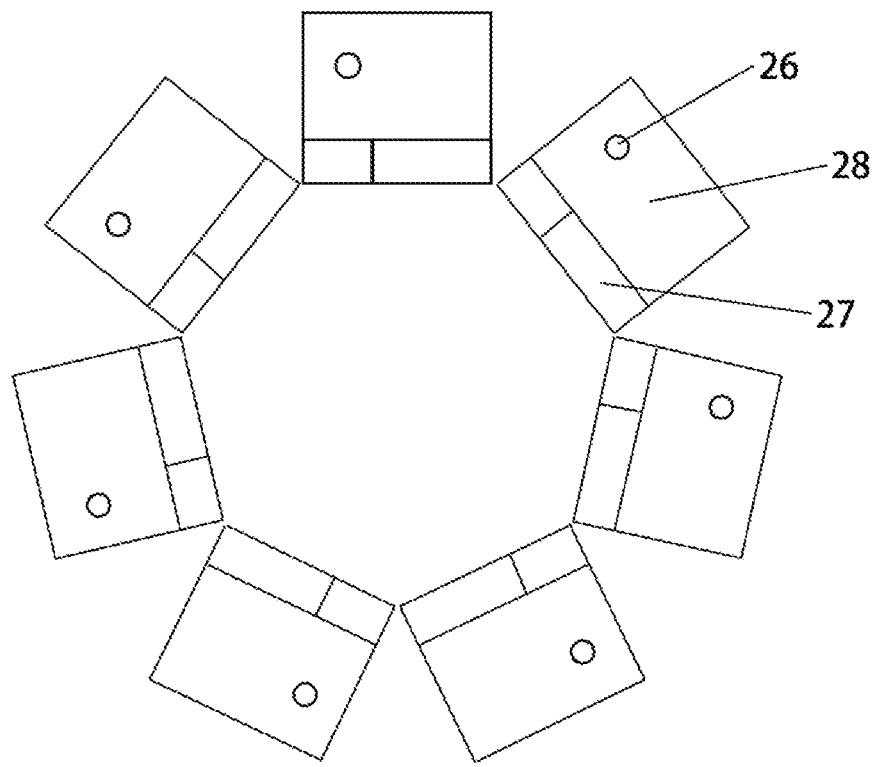
FIG. 6 is a plan view of an annular array of greenhouse bodies according to embodiment 3 of the present invention.

In embodiment 3, as shown in FIG. 6, the greenhouse bodies are arranged in an annular array, their pupae rooms 27 are located in the inner periphery, and the mating and oviposition rooms 28 are located in the outer periphery. This ensures that the mating and oviposition rooms have plenty of sunlight.

Finally, it should be noted that the above embodiments are only used to illustrate the technical solutions of the present invention and not to limit the scope of protection of the present invention. Although the present invention is described in detail with reference to the preferred embodiments, those skilled in the art should understand that the technical solutions of the present invention may be modified or equivalently replaced without departing from the spirit and scope of the technical solutions of the present invention.

What is claimed is:

1. A large-scale and multi-span breeding greenhouse for adult black soldier flies, comprising greenhouse bodies, characterized in that each greenhouse body comprises a pupae room and a mating and oviposition room; a partition wall is provided between the pupae room and the mating and oviposition room, the partition wall is provided with a door hole communicating the pupae room and the mating and oviposition room; the pupae room is opaque; the greenhouse body further comprises a light guiding device which introduces sunlight into the mating and oviposition room.

2. The large-scale, multi-span breeding greenhouse for adult black soldier flies according to claim 1, characterized in that a wall of the greenhouse bodies consists of a color steel plate, film or a cement brick wall.

3. The large-scale, multi-span breeding greenhouse for adult black soldier flies according to claim 2, characterized in that the wall of the greenhouse body comprises a first wall and a second wall, the first wall forms a wall of the mating and oviposition room with the partition wall, the second wall forms a wall of the pupae room with the partition wall.

4. The large-scale, multi-span breeding greenhouse for adult black soldier flies according to claim 3, characterized in that the light guiding device comprises a light transmitting window, which is arranged on the first wall, and light transmitting boards, which are embedded on a roof of the mating and oviposition room; the inside of the light transmitting window is provided with a detachable gauze; the light transmitting boards are arranged disjointedly.

5. The large-scale, multi-span breeding greenhouse for adult black soldier flies according to claim 4, characterized in that the light guiding device comprises an auto-tracking reflector, which reflects sunlight into the mating and oviposition room, and/or a light guiding lighting system, which introduces sunlight into the mating and oviposition room.

6. The large-scale, multi-span breeding greenhouse for adult black soldier flies according to claim 4, characterized in that the greenhouse body is further provided with a temperature and humidity control system, the temperature and humidity control system includes a shading net for controlling the light transmitting area of the light transmitting window and the light transmitting board, a negative pressure exhaust fan installed on the first wall, a radiator installed in the pupae room and the mating and oviposition room, a first spraying device and an air conditioner both installed in the mating and oviposition room, and a second spraying device installed above the greenhouse body.

7. The large-scale, multi-span breeding greenhouse for adult black soldier flies according to claim 1, characterized in that the light guiding device comprises an auto-tracking reflector, which reflects sunlight into the mating and oviposition room, and/or a light guiding lighting system, which introduces sunlight into the mating and oviposition room.

8. The large-scale, multi-span breeding greenhouse for adult black soldier flies according to claim 1, characterized in that the mating and oviposition room is provided with an egg collecting device and an attaching material for the attachment of black soldier flies.

9. The large-scale, multi-span breeding greenhouse for adult black soldier flies according to claim 8, characterized in that the egg collecting device comprises a stand, an oviposition plate provided on the stand, and an oviposition-inducing material placed on the oviposition plate.

10. The large-scale, multi-span breeding greenhouse for adult black soldier flies according to claim 8, characterized in that the attaching material is an artificial plant and/or cloth stripe and/or fibrous stripe suspended in the mating and oviposition room.

11. The large-scale, multi-span breeding greenhouse for adult black soldier flies according to claim 1, characterized in that the greenhouse bodies are arranged in an annular array or in a row, and the greenhouse bodies are connected to each other or arranged disjointedly; when the greenhouse bodies are in an annular array, the pupae room is located in the inner periphery of the greenhouse bodies; the breeding greenhouse further comprises a buffer room which is connected to the pupae room, the buffer room is provided in the greenhouse body or between two greenhouse bodies.

* * * * *